US008025055B1

(12) United States Patent
Grady

(10) Patent No.: US 8,025,055 B1
(45) Date of Patent: Sep. 27, 2011

(54) CPAP ENCLOSURE FOR THE TREATMENT OF BREATHING DISORDERS

(76) Inventor: Daniel J. Grady, Southern Pines, NC (US)

( * ) Notice: Subject to any disclaimer, the term of this patent is extended or adjusted under 35 U.S.C. 154(b) by 1020 days.

(21) Appl. No.: 11/870,496

(22) Filed: Oct. 11, 2007

Related U.S. Application Data

(63) Continuation-in-part of application No. 10/404,638, filed on Apr. 1, 2003, now Pat. No. 7,520,277.

(51) Int. Cl.
*A61M 11/00* (2006.01)
(52) U.S. Cl. .............................. 128/205.26; 128/204.18
(58) Field of Classification Search ............ 128/204.18, 128/205.26, 205.27, 200.24, 202.12
See application file for complete search history.

(56) References Cited

U.S. PATENT DOCUMENTS

| | | | |
|---|---|---|---|
| 4,011,866 A * | 3/1977 | Klein et al. ............... | 128/204.21 |
| 5,799,652 A | 9/1998 | Kotliar | |
| 5,850,833 A | 12/1998 | Kotliar | |
| 5,887,439 A | 3/1999 | Kotliar | |
| 5,924,419 A | 7/1999 | Kotliar | |
| 5,964,222 A | 10/1999 | Kotliar | |
| 6,805,120 B1 * | 10/2004 | Jeffrey et al. ............ | 128/204.23 |
| 2001/0035185 A1 * | 11/2001 | Christopher ............. | 128/204.17 |

FOREIGN PATENT DOCUMENTS

| | | |
|---|---|---|
| CA | 2227444 | 2/1997 |
| EP | 959862 | 11/2001 |

OTHER PUBLICATIONS

HYPOXICO Home Products, http://www.hypoxico.com/home_sleep.htm, 3 pages.
HYPOXICO More Information, http://www.hypoxico.com/info.htm, 2 pages.

* cited by examiner

*Primary Examiner* — Steven Douglas
(74) *Attorney, Agent, or Firm* — Coats & Bennett, P.L.L.C.

(57) ABSTRACT

A CPAP enclosure used in the treatment of breathing disorder comprises a base connected to a bed, a canopy connected to the base, and a sealing member that connects the canopy to the base. The sealing member forms a substantially airtight seal such that the canopy and the base form a substantially airtight enclosure around at least a portion of the bed. A Continuous Positive Airway Pressure (CPAP) compressor connects to the enclosure via flexible tubing, and generates a continuous positive airway pressure within the enclosure to treat a patient. A blender blends one or more compressed gasses with the compressed air from the CPAP compressor for delivery to the enclosure.

25 Claims, 7 Drawing Sheets

CPAP ENCLOSURE FOR THE TREATMENT OF BREATHING DISORDERS

RELATED APPLICATIONS

This application is a continuation-in-part of co-pending U.S. patent application Ser. No. 10/404,638 filed Apr. 1, 2003, titled "CPAP Enclosure for the Treatment of Sleep Apnea," which is incorporated herein by reference in its entirety.

BACKGROUND OF THE INVENTION

The present invention relates generally to medical devices, and in particular, to medical devices used in the treatment of breathing disorders.

Breathing disorders affect a large number of people. Obstructive Sleep Apnea (OSA), for example, is a type of sleep disorder that produces altered breathing functions during sleep. Patients who suffer from OSA experience a partial or complete airway obstruction during sleep, resulting in decreased airflow and sleep fragmentation. This adversely affects respiratory, cardiac, and neurological functions, and often causes patients to experience excessive daytime drowsiness. When left untreated, OSA may result in long-term health problems such as hypertension, stroke, cardiac arrhythmias, and myocardial infarction.

One way to treat patients suffering from breathing disorders is to apply a Continuous Positive Airway Pressure (CPAP) to the patient. The positive pressure functions as a pneumatic stent that prevents the collapse of the upper airway. Current devices typically apply CPAP by way of a mask secured to the patient's head. While effective, such treatment is not without problems. For example, masks may result in irritation, nasal congestion, and nosebleeds. Other side effects may include a loss of positive pressure from displaced or poorly fitted masks. These side effects, and others like them, may be factors that contribute to the relatively low percentage of patient compliance with current CPAP treatments. Therefore, there is a need for an improved system and method of administering CPAP to patients suffering from breathing disorders.

SUMMARY OF THE INVENTION

A CPAP enclosure used in the treatment of breathing disorders comprises an airtight enclosure that surrounds at least a portion of a bed. The enclosure includes a base, a canopy connected to the base, and a sealing member that connects the canopy to the base. The sealing member forms a substantially airtight seal between the canopy and the base. A Continuous Positive Airway Pressure (CPAP) compressor connects to the enclosure via flexible tubing, and generates a continuous positive airway pressure within the enclosure to treat a patient.

In one embodiment, the patient enters the enclosure through an access door, lies down on the bed, and seals the access door closed. The CPAP compressor generates the continuous positive airway pressure within the enclosure, which may be regulated by a pressure valve and monitored using a manometer. The continuous positive pressure prevents collapse of the patient's upper airway.

Breathing disorders such as sleep apnea, adult respiratory distress syndrome, pneumonia, hypoxemic respiratory failure, and influenza can be treated with CPAP.

DETAILED DESCRIPTION OF THE INVENTION

Figure 1:
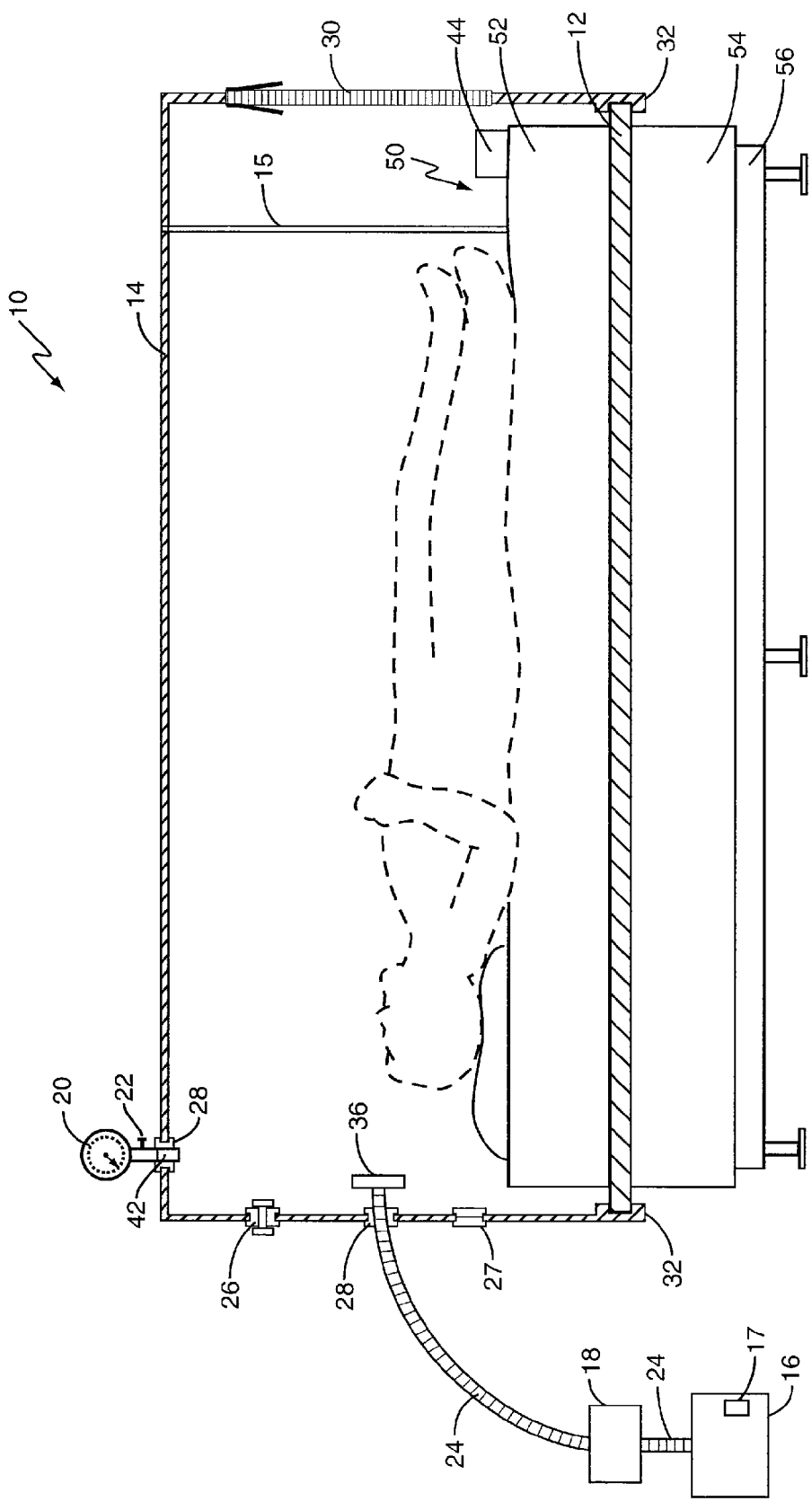
FIG. 1 illustrates a patient afflicted with a breathing disorder using one embodiment of the present invention.

Referring now to FIG. 1, the CPAP enclosure of the present invention is shown therein and indicated generally by the number 10. CPAP enclosure 10 comprises a base 12, a canopy 14 releasably coupled to the base 12, and a CPAP compressor 16. A first sealing member 32 couples the base 12 to the canopy 14, and forms a substantially airtight seal between canopy 14 and base 12. When base 12 is coupled to canopy 14, a substantially air-tight sleep enclosure 10 is formed that extends around at least a portion of bed 50.

Inlet hose 24 comprises a flexible non-kink tubing, and connects compressor 16, an optional humidifier 18, and a manometer 20 to enclosure 10 through one or more airtight ports 28 disposed in the sidewalls of canopy 14. The humidifier 18 conditions the air output by compressor 16 by controlling its relative humidity. The inspired air may further be temperature controlled, if desired, by one or more heated wires (not shown) within the flexible tubing of inlet hose 24. The manometer 20 monitors the air pressure within the enclosure. As seen in the figures, manometer 20 connects to the enclosure 10; however, this particular configuration is not required. In some embodiments, manometer 20 may be integrated with the compressor 16.

A T-adaptor 36 is disposed within enclosure 10. As seen in later embodiments, one or more heat exchange filters may be optionally disposed on the T-adaptor 36. However, this is not required. In other embodiments, such as those that administer an aerosol into enclosure 10, the compressor 16 may include heat exchange filters. Expired air containing carbon dioxide, for example, exits the enclosure 10 through a filter 42. In one embodiment, filter 42 comprises a High Efficiency Particulate Air (HEPA) filter capable of filtering particulates, viruses, and/or bacteria to prevent contamination outside the enclosure 10.

Canopy 14 may be constructed from a lightweight, flexible, non-allergenic, puncture resistant material, such as acrylic, polyethylene, or 18-gauge PVC with vinyl, although it should be understood that canopy 14 is not limited only to these materials. Further, the material used to construct canopy 14 may attenuate sound and/or light to facilitate sleeping, and may be constructed as a single piece, or alternatively, may comprise a plurality of panels fused together. The material used for the canopy 14 may be sufficiently rigid so as to be substantially self-supporting absent continuous pressure inside the canopy 14. Alternatively, canopy 14 may be made of a flexible sheet material having one or more rigid supports that prevent the collapse of canopy 14 in the event of sudden depressurization.

One or more airtight ports 28 formed in the sidewalls of canopy 14 maintain positive air pressure within enclosure 10, while providing access for inlet hose 24, various wires and cables that lead to equipment used in diagnostic studies, and cables used by specialty beds. Further, one or more emergency one-way air intake valves 26 may also be disposed in the sidewall of canopy 14. The one-way air intake valves 26 are designed to open should enclosure 10 experience a sudden depressurization and/or failure of compressor 16. The air intake valve 26 should be operable to provide a patient with an adequate supply of fresh air, and prevent inadvertent suffocation of the patient. A high-pressure relief valve 27 may also be disposed in a sidewall of the canopy 14 to prevent excessive pressure buildup within the enclosure 10. Particularly, the high-pressure relief valve 27 will open to vent excess pressure outside the enclosure 10 when the pressure inside the canopy 14 exceeds the therapeutic CPAP pressure.

FIG. 1 illustrates one embodiment wherein base 12 is disposed between the mattress 52 and boxspring 54 of a bed, and projects outward from the periphery of mattress 52. Base 12 may be constructed of an airtight acrylic or plastic material, and may be formed as a single piece or a plurality of panels that are fitted together. In this embodiment, the first sealing member 32, constructed of rubber or other elastic material, is connected to the bottom edge of canopy 14. When mated with base 12, the first sealing member 32 forms a substantially airtight seal between base 12 and canopy 14. This airtight seal permits canopy 14 and base 12 to form the substantially airtight sleeping enclosure 10 around at least a portion of bed 50.

A patient being treated for a breathing disorder such as OSA, for example, may access enclosure 10 through an access door disposed in a sidewall of canopy 14. In this embodiment, the access door comprises a double-sided zipper 30 operable from both inside and outside of enclosure 10, and seals enclosure 10 so that it remains substantially airtight. In other embodiments, however, the access door comprises a rigid door (not shown) that hingedly connects to the enclosure 10. With these embodiments, the positive pressure within the canopy 14 maintains the door in a closed position and sealed. Other embodiments may include a "ZIP-LOC" type zipper (not shown), or the two-way type of seal used in underwater wetsuits (not shown). Whatever type of zipper or seal is used, it should permit a patient to operate it from both inside and outside enclosure 10.

The CPAP compressor 16 is connected to an external power source (not shown), and generates a continuous positive airway pressure used to treat patients with breathing disorders. CPAP compressor 16 operates by compressing a gas (e.g., air), and delivering it to the interior of enclosure 10 via inlet hose 24. A microprocessor 17 may be used to vary the pressure and/or flowrate as needed or desired. The compressor 16 is capable of generating the continuous positive airway pressure in a range much lower than that of known hyperbaric chambers. In one embodiment, compressor 16 generates a continuous positive airway pressure within enclosure 10 in the low range of about 0-40 cm. $H_2O$, and preferably in the range of about 0-30 cm $H_2O$. Although these ranges are exemplary, those skilled in the art will realize that the pressures created by compressor 16 are radically lower than the pressures of 2000-3000 cm. $H_2O$ typically created by known hyperbaric chambers. These higher pressures found in hyperbaric chambers require the chambers to be built of heavy, often multi-layered and expensive materials that can withstand intense pressure. Further, the high pressures generated by known hyperbaric chambers generally require prolonged periods for decompression for entry/exit from the enclosure, and generate very high noise levels. Thus, they are unsuitable for treating at least some types of breathing disorders such as OSA and other sleep related breathing disorders.

Compressor 16 may be turbine driven to reduce noise generation, and further, may be capable of generating airflow rates that exceed four times the patient's exhaled minute volume. In one embodiment, this produces a total airflow through the enclosure 10 of about 1-100 liters/minute, and preferably 1-40 liters/minute. This range of airflow rate through enclosure 10 effectively flushes the patient's exhaled carbon dioxide to the outside atmosphere, and helps reduce re-breathing of exhaled gasses. Further, the flow rate from compressor 16 is adjustable to completely prevent carbon dioxide re-breathing, as well as to facilitate certain types of patient monitoring in a diagnostic lab, for example, capnography monitoring. In some embodiments, a carbon dioxide absorbent device 44, such as a scrubber, may be disposed within the enclosure 10 to minimize re-breathing of carbon dioxide. The carbon dioxide absorbent device 44 may comprise, for example, material such as soda lime or calcium hydroxide.

Figure 2:
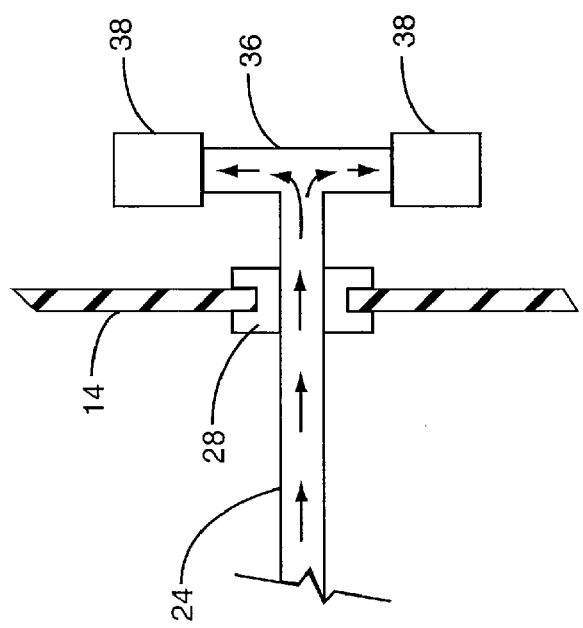
FIG. 2 illustrates an exemplary T-adaptor used in one embodiment of the present invention.

The compressor 16 connects to a T-adapter 36 that lies within enclosure 10 via inlet hose 24 that passes through the airtight port 28. As seen in FIG. 2, the T-adapter 36 may include one or more heat-moisture exchange filters 38 to maintain sound and humidity at acceptable levels within enclosure 10. One type of T-adapter 36 used in the present invention is a standard Briggs T-adapter, although those skilled in the art will readily appreciate that other types of adapters 36 may also be used.

Figure 3:
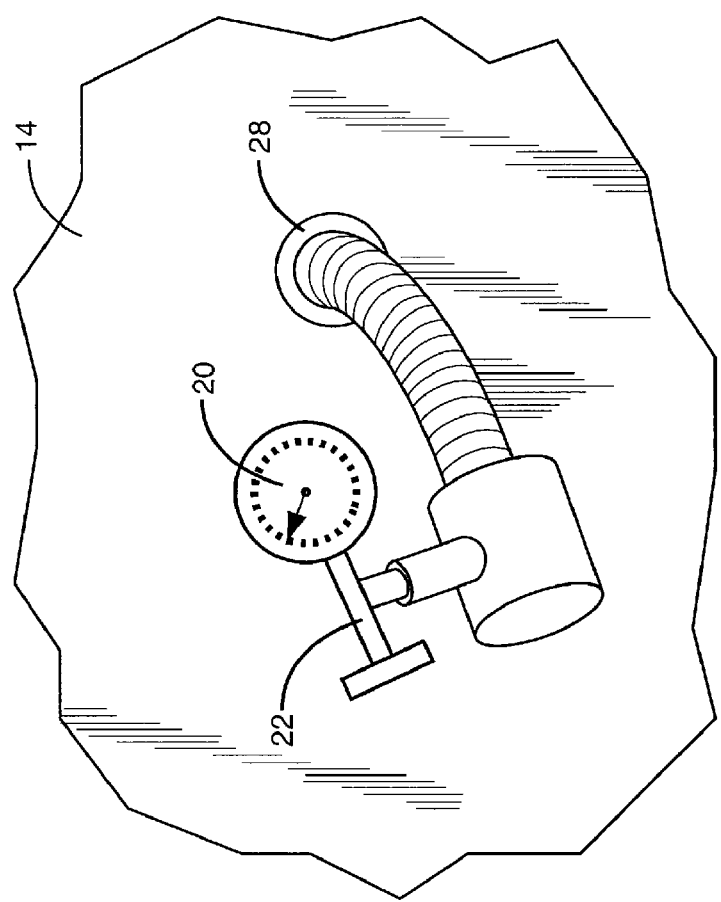
FIG. 3 illustrates an exemplary manometer and pressure valve used in one embodiment of the present invention.

A manometer 20, shown in FIG. 3, is used to monitor the continuous positive airway pressure inside enclosure 10. As previously stated, the manometer 20 may be connected to the canopy 14 or included with compressor 16. A variable pressure release valve 22 regulates the amount of positive pressure by restricting the opening in which the air inside enclosure 10 can exit. In one embodiment, manometer 20 and valve 22 are shown as a single entity, and are connected to a sidewall of canopy 14 via flexible tubing. However, those skilled in the art will readily understand that manometer 20 and valve 22 may exist as separate parts, and further, may connect to enclosure 10 through airtight ports 28 in either the canopy 14 or base 12.

Figure 4:
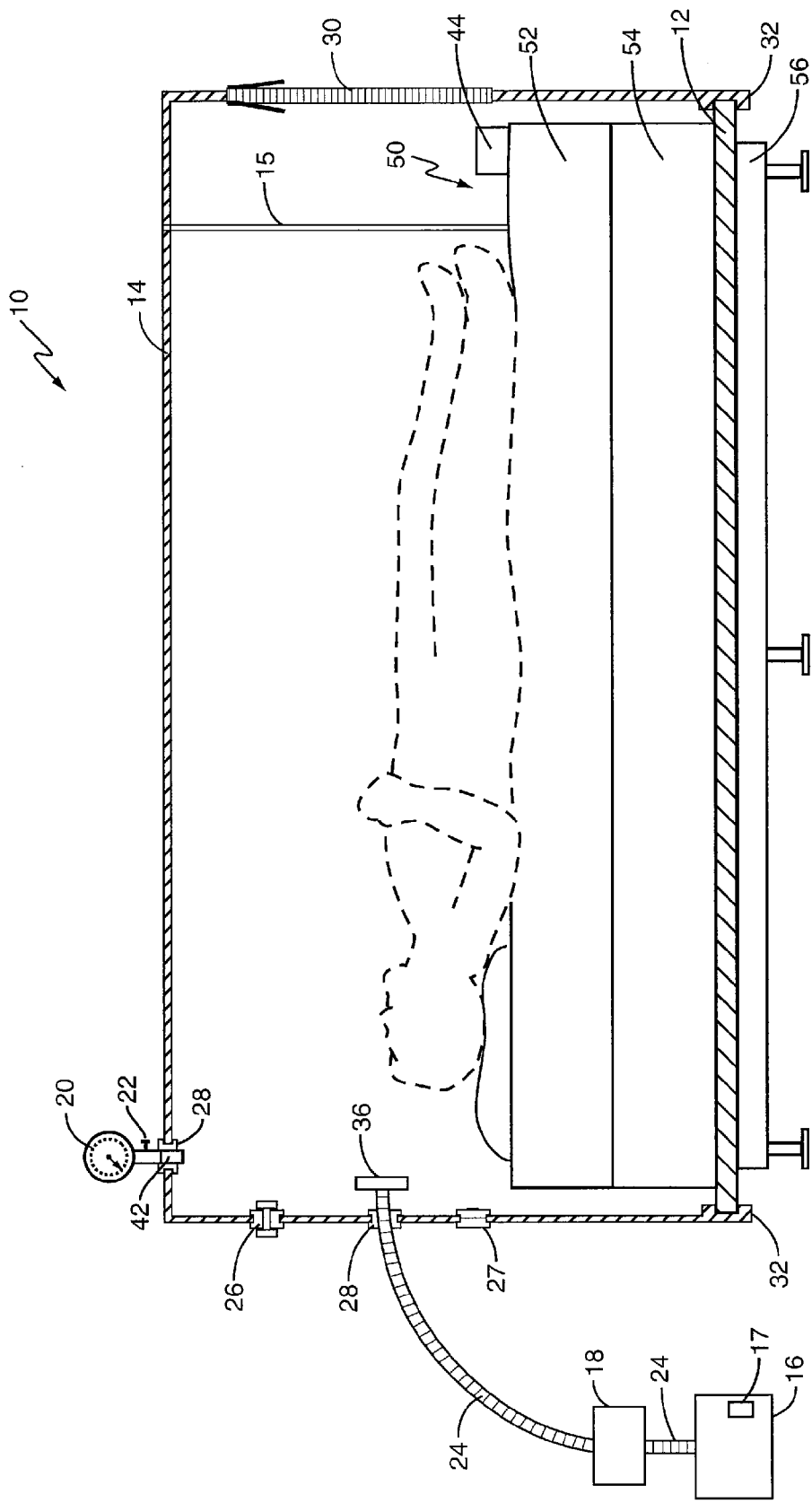
FIG. 4 illustrates the patient using an alternate embodiment of the present invention.

FIG. 4 illustrates an alternate embodiment of the present invention wherein base 12 is disposed between the boxspring 54 and the frame of the bed 56. The first sealing member 32 is disposed on the bottom edges of canopy 14, and forms the substantially airtight seal with base 12. More specifically, the first sealing member 32 engages the outer edge of base 12 to form an airtight seal. Although the position of base 12 may vary, those skilled in the art will understand that this does not adversely affect the operability of enclosure 10. That is, the first sealing member 32 disposed on the bottom edges of canopy 14 forms the substantially airtight seal between the canopy 14 and base 12. As such, the canopy 14 and base 12 form the substantially airtight sleeping enclosure 10 around at least a portion of the patient's bed 50.

Figure 5:
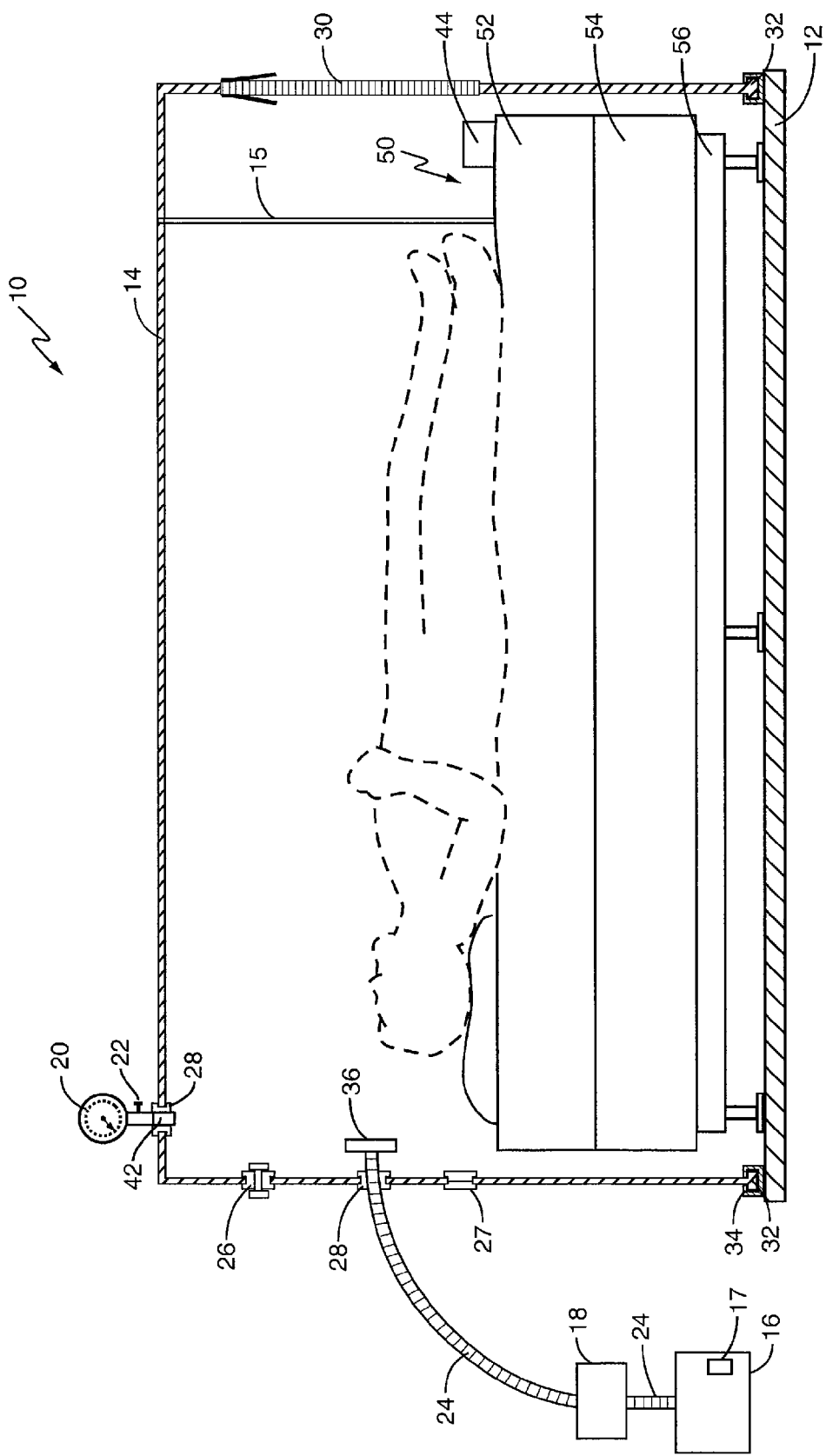
FIG. 5 illustrates the patient using yet another embodiment of the present invention.

In another alternate embodiment shown in FIG. 5, base 12 is positioned under the frame 56 of bed 50. In this embodiment, the first sealing member 32 mates with a second sealing member 34 disposed on base 12, and forms the substantially airtight seal around base 12. The position of base 12 in this embodiment creates a substantially airtight enclosure 10 around the patient's entire bed.

Those skilled in the art will appreciate that base 12 need not be secured or attached to bed 50. However, depending on the type of bed 50 that enclosure 10 encloses, it may be more efficient to secure base 12 to bed 50. For example, it may be sufficient to simply dispose base 12 between the mattress 52 and boxspring 54, or between the boxspring 54 and frame 56, in a typical bed 50. In these embodiments, the weight of the patient together with the weight of the mattress 52 and/or boxspring 54 may be sufficient to stabilize the base 12 and prevent it from shifting or moving. Thus, inadvertent radical movement by the patient will not compromise the airtight seal around base 12.

However, other embodiments may be better adapted for situations where enclosure 10 is required to enclose specialty beds (e.g., beds that are operable to elevate all or a portion of the mattress 52, provide percussion, or rotate the patient for postural drainage such as those found in hospitals and diagnostic labs). In these cases, mechanical fasteners (not shown) may be used to secure base 12 to frame 54, and therefore stabilize base 12 regardless of the position of the mattress 52. Whatever the embodiment, enclosure 10 should form a substantially airtight enclosure around at least a portion of bed 50, and provide the patient with an enclosure that is comfortable and has adequate area in which to move freely.

Figure 6A:
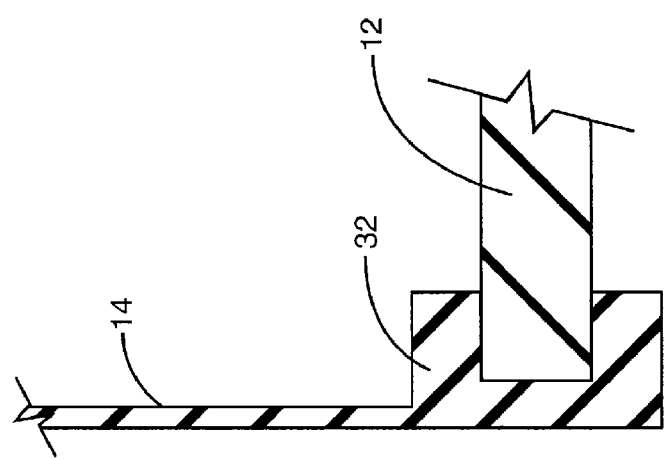
FIGS. 6A-6C illustrate exemplary sealing members used in various embodiments of the present invention.
Figure 6B:
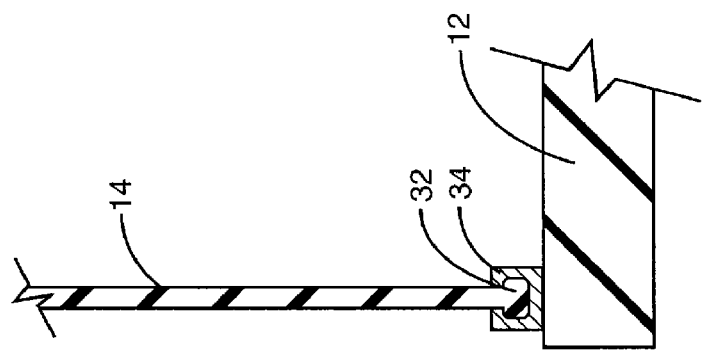
Figure 6C:
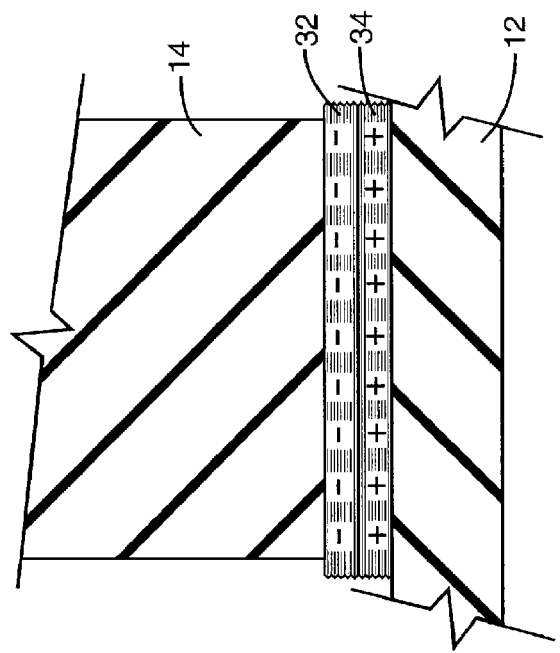

FIGS. 6A-6C illustrate various configurations for the first and second sealing members 32, 34. FIG. 6A illustrates one embodiment of the first sealing member 32 connected to the bottom edges of canopy 14, thereby terminating the sidewalls of canopy 14. The first sealing member 32 is elastic and substantially U-shaped, and receives the outer edges of base 12. To form the airtight seal between canopy 14 and base 12, a patient merely pushes the first sealing member 32 onto the edges of base 12.

FIG. 6B illustrates the first and second sealing members 32, 34 that may be used in the embodiment of FIG. 5, for example. Here, first sealing member 32 is shaped differently, but still terminates the bottom edges of canopy 14. The second sealing member 34 is disposed on the base 12, and receives the first sealing member 32 in a manner similar to that of a "ZIP-LOC" seal. That is, a user aligns the first and second sealing members 32, 34, and pushes the first sealing member 32 into the receiving portion of second sealing member 34. In some embodiments, the first sealing member 32 may be slightly rigid to facilitate insertion of the first and second sealing members 32, 34.

Another embodiment of the first and second sealing members 32, 34 is shown in FIG. 6C. In this embodiment, the first and second sealing members 32, 34 are disposed on the bottom edge of canopy 14 and base 12, respectively, but assume the form of magnetic rubber strips having opposing polarities. The opposite polarities of the first and second sealing members 32, 34 attract each other, thereby forming the substantially airtight seal around between canopy 14 and base 12. Thus, base 12 and canopy 14 forms the substantially airtight enclosure 10.

To treat a person afflicted with a breathing disorder, such as OSA, the user first forms the enclosure 10 by coupling the canopy 14 to base 12, and forming a substantially airtight enclosure that surrounds at least a portion of the patient's bed 50. The first and/or second sealing members form the substantially airtight seal between the canopy 14 and base 12, as described above. The patient, or another user, operates compressor 16 such that it generates a positive air pressure within enclosure 10. Once a desired pressure is reached, the patient enters through the access door, and closes the double-sided zipper 30. The patient is now free to lie down and sleep or relax while the CPAP compressor 16 generates and maintains a continuous positive airway pressure within the interior of enclosure 10. In some embodiments, protective gloves (not shown) may be integrated into the sidewall of canopy 14. This would allow a medical professional or other person to treat a patient within enclosure 10 without disrupting the substantially airtight seal.

Figure 7:
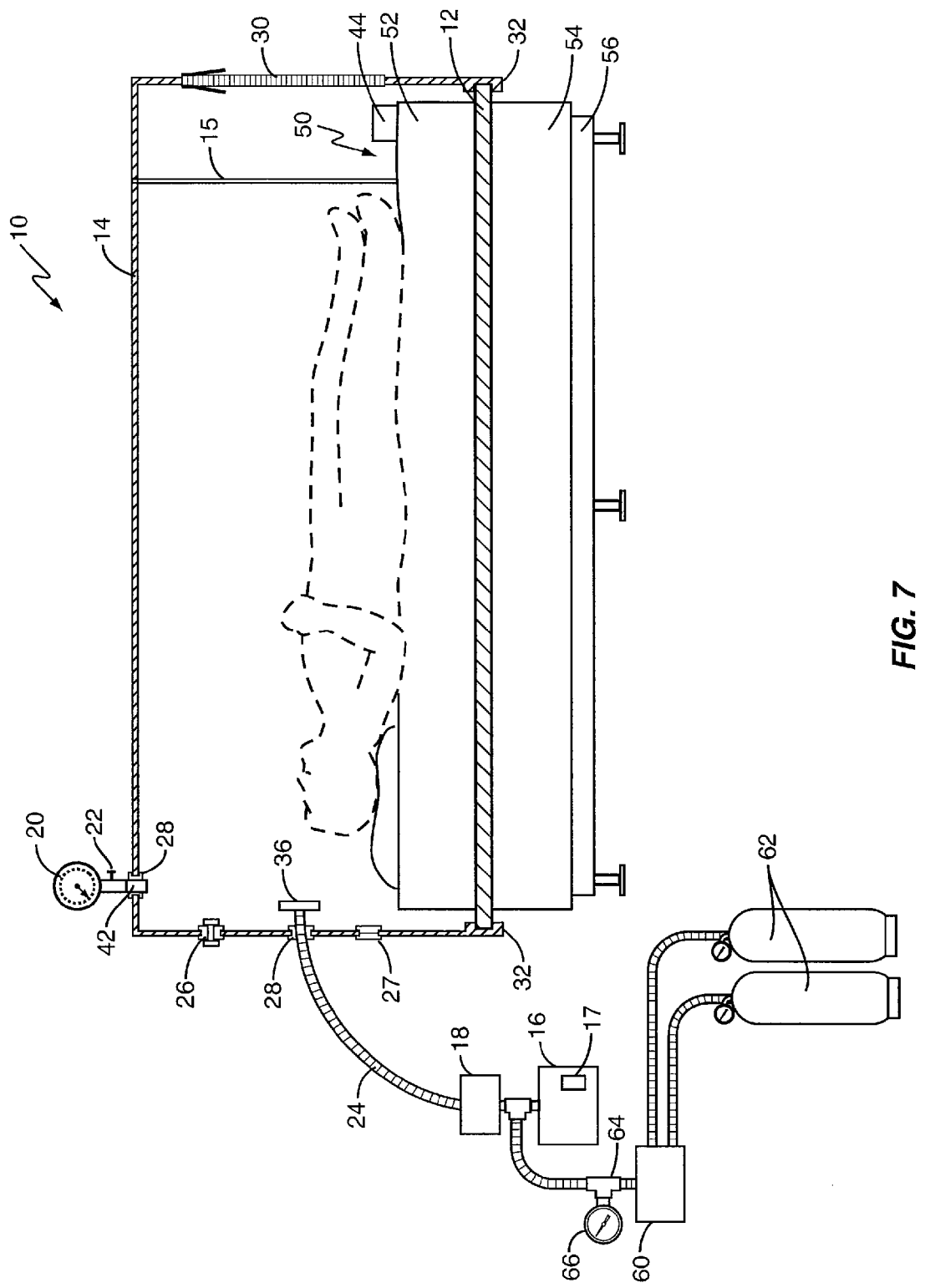
FIG. 7 illustrates the patient using another embodiment of the present invention.

Those skilled in the art will readily appreciate many variations may be made to the present without departing from its scope. For one, the CPAP compressor may deliver other types of gases and/or gas mixtures to the interior of enclosure 10 in addition to (or in place of) air. FIG. 7, for example, illustrates one embodiment wherein gas mixtures other than compressed air are utilized to treat a patient. Particularly, various oxygen concentrations may be delivered to a patient within the CPAP enclosure 10 by mixing compressed gases with air, and injecting the mixture into the enclosure 10.

In addition, compressors capable of delivering other types of non-invasive ventilation may be utilized. In one embodiment, for example, compressor 16 comprises a Bi-Level Positive Airway Pressure (BiPAP®) compressor. BiPAP® compressors provide two levels of air pressure for a patient within the enclosure 10. A first level is provided during inhalation and a second, lower pressure is provided during exhalation. The pressure levels and/or flowrates may be controlled, for example, by microprocessor 17. Providing different levels of pressure may help in exchanging carbon dioxide and oxygen.

As seen in FIG. 7, a gas blender 60 receives compressed gases such as oxygen from one or more tanks 62, and mixes the gases for delivery to inlet hose 24 via a T adapter 64. A gas flow meter 66 may be used to control the mixture to include a selected oxygen concentration, and to control the flow of the mixed gases into the inlet hose 24. The blended gas mixture may be mixed with the compressed air provided by compressor 16 and flows into humidifier 18. The resultant humidified gas mixture then enters enclosure 10 as previously described. The gas mixture entering enclosure 10 contains the desired oxygen concentration, which may be verified using an oxygen analyzer or similar measuring tool disposed proximate to patient's airway.

Although FIG. 7 shows oxygen being mixed with air to form an oxygen-rich mixture, those skilled in the art will appreciate that other gases may also be mixed with air. For example, gas mixtures such as helium and/or oxygen may be blended with air and delivered to enclosure 10. Alternatively, pure oxygen, or oxygen blended with other gases, could be delivered to the enclosure.

Figure 8:
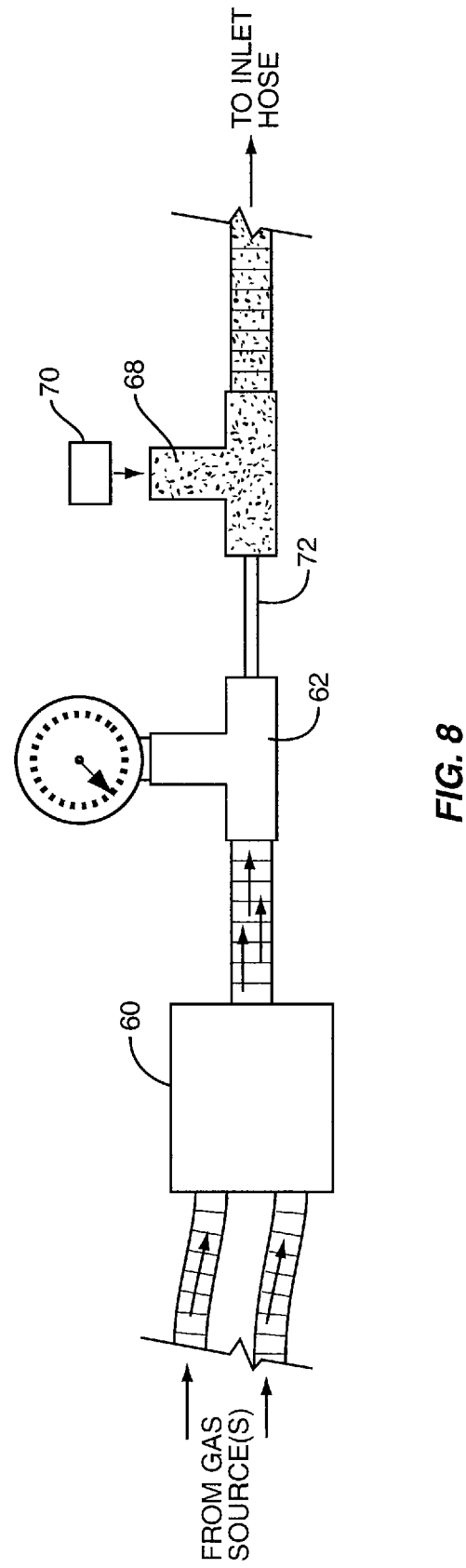
FIG. 8 illustrates another embodiment wherein medicines are aerosolized for injection into an enclosure according to one embodiment of the present invention.

FIG. 8 illustrates another embodiment wherein medications are aerosolized and delivered to enclosure 10 for inhalation by the patient. A nebulizer device 68 connects to the inlet hose 24. The nebulizer 68 receives a container 70 of liquid medicine, and creates an aerosol when the liquid medicine is forced through a small bore tubing 72. The small bore tubing 72 may be connected to gas blender 60 and the flow meter 66. The mixed gas flows from blender 60 through flow meter 62, and into the small bore tubing 72 of nebulizer 68. The aerosolized medication from nebulizer 68 is then mixed with the blended gases and delivered with the blended gases into enclosure 10 via the inlet hose 24 and air-tight port 28. Exhaled aerosol and other waste gases, such as carbon dioxide, may exit enclosure 10 as previously described.

The embodiments illustrated in the drawings show the canopy 14 permitting access into the enclosure via the airtight ports 28. However, the one-way air intake valve 26 and air-tight ports 28 may actually be disposed in either the base 12 or canopy 14 or both. Additionally, those skilled in the art will appreciate that any known mechanical fastener, for example, bolts and/or screws, may be used to secure to the bed frame 56.

The present invention may of course, be carried out in other specific ways than those herein set forth without departing from the essential characteristics of the invention. The present embodiments are, therefore, to be considered in all respects as illustrative and not restrictive and all changes coming within the meaning and equivalency range of the appended claims are intended to be embraced therein.

What is claimed is:

1. A CPAP enclosure for treating a patient comprising:
a substantially air-tight enclosure surrounding at least a portion of a bed;
a blender configured to produce a blended gas to be delivered to the enclosure; and
a Continuous Positive Airway Pressure (CPAP) compressor coupled to the enclosure and the blender, and configured to:
generate a continuous positive airway pressure within the enclosure; and
deliver the blended gas to the enclosure at the continuous positive airway pressure.

2. The CPAP enclosure of claim 1 wherein the blender is configured to produce the blended gas from compressed gasses received from one or more gas storage tanks.

3. The CPAP enclosure of claim 2 wherein the CPAP compressor is configured to deliver the blended gas mixed with compressed air to the enclosure at the continuous positive airway pressure.

4. The CPAP enclosure of claim 1 further comprising a nebulizer connected to the enclosure, the nebulizer comprising a tube to aerosolize a medication being delivered to the enclosure.

5. The CPAP enclosure of claim 1 further comprising a filter to prevent particulate matter within the enclosure from contaminating the ambient environment.

6. The CPAP enclosure of claim 5 wherein the filter comprises a High Efficiency Particulate Air (HEPA) filter.

7. The CPAP enclosure of claim 1 further comprising a scrubber to remove carbon dioxide from within the enclosure.

8. The CPAP enclosure of claim 1 wherein the CPAP compressor is configured to deliver the blended gas at a rate sufficient with which to substantially prevent the patient from rebreathing exhaled carbon dioxide.

9. The CPAP enclosure of claim 8 wherein the CPAP compressor is configured to deliver the blended gas mixed with compressed air to the enclosure at a flowrate of about 1-100 liters per minute.

10. The CPAP enclosure of claim 1 wherein the substantially air-tight enclosure comprises a canopy that attenuates light and sound.

11. The CPAP enclosure of claim 1 further comprising a high pressure relief valve disposed on the enclosure.

12. The CPAP enclosure of claim 1 wherein the CPAP compressor is configured to generate a plurality of different continuous airway pressures within the CPAP enclosure.

13. A method of treating a patient having a breathing disorder, the method comprising:
forming a substantially airtight enclosure around at least a portion of a patient's bed;
blending a gas to be delivered to the enclosure; maintaining a continuous positive airway pressure within the enclosure to treat the patient having the breathing disorder; and
delivering the blended gas to the enclosure at the continuous positive airway pressure.

14. The method of claim 13 wherein blending a gas to be delivered to the enclosure comprises blending the gas from one or more compressed gasses received from one or more gas storage tanks.

15. The method of claim 14 wherein delivering the blended gas to the enclosure at the continuous positive airway pressure comprises mixing the blended gas with compressed air, and delivering the mixture to the enclosure at the continuous positive airway pressure.

16. The method of claim 14 further comprising varying a flow of the blended gas into the enclosure.

17. The method of claim 15 further comprising humidifying the blended gas and compressed air mixture.

18. The method of claim 13 further comprising aerosolizing a medication, and delivering the aerosolized medication to the enclosure.

19. The method of claim 13 further comprising filtering gasses within the enclosure to prevent particulate matter within the enclosure from contaminating the ambient environment.

20. The method of claim 13 further comprising scrubbing carbon dioxide from within the enclosure.

21. The method of claim 13 further comprising delivering the blended gas to the enclosure at a flowrate that is sufficient with which to substantially prevent the patient from rebreathing exhaled carbon dioxide.

22. The method of claim 13 wherein the flowrate is about 1-100 liters per minute.

23. The method of claim 13 wherein the substantially airtight enclosure comprises a canopy that attenuates light and sound.

24. The method of claim 13 further comprising controlling a flowrate of the compressor.

25. The method of claim 13 wherein maintaining a continuous positive airway pressure within the enclosure comprises delivering the blended gasses to within the enclosure at different positive pressures.

* * * * *